United States Patent
Utro et al.

(10) Patent No.: US 11,238,955 B2
(45) Date of Patent: *Feb. 1, 2022

(54) SINGLE SAMPLE GENETIC CLASSIFICATION VIA TENSOR MOTIFS

(71) Applicant: International Business Machines Corporation, Armonk, NY (US)

(72) Inventors: Filippo Utro, Pleasantville, NY (US); Aldo Guzman Saenz, White Plains, NY (US); Chaya Levovitz, New York, NY (US); Laxmi Parida, Mohegan Lake, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 989 days.

This patent is subject to a terminal disclaimer.

(21) Appl. No.: 15/900,048

(22) Filed: Feb. 20, 2018

(65) Prior Publication Data

US 2019/0258776 A1     Aug. 22, 2019

(51) Int. Cl.
*G06N 20/00* (2019.01)
*G16B 20/00* (2019.01)
(Continued)

(52) U.S. Cl.
CPC .............. *G16B 20/00* (2019.02); *G06N 7/005* (2013.01); *G06N 20/00* (2019.01); *G16B 40/00* (2019.02); *G16H 50/20* (2018.01)

(58) Field of Classification Search
CPC ........ G16B 20/00; G16B 40/00; G16B 40/20; G16B 50/30; G06N 20/00; G06N 7/005;
(Continued)

(56) References Cited

U.S. PATENT DOCUMENTS

| 8,340,437 B2 | 12/2012 | Abramoff et al. |
| 9,773,311 B2 | 9/2017 | Ross et al. |

(Continued)

FOREIGN PATENT DOCUMENTS

WO    2008066596 A2    5/2008

OTHER PUBLICATIONS

Lou, Y. et al., "Tensor factorization toward precision medicine", Brief Bioinform, May 1, 2017;18(3):511-514. 12 pages.

(Continued)

*Primary Examiner* — Dave Misir
(74) *Attorney, Agent, or Firm* — Cantor Colburn LLP; Kristofer Haggerty

(57) ABSTRACT

A computer-implemented method includes generating, by a processor, a set of training data for each phenotype in a database including a set of subjects. The set of training data is generated by dividing genomic information of N subjects selected with or without repetition into windows, computing a distribution of genomic events in the windows for each of N subjects, and extracting, for each window, a tensor that represents the distribution of genomic events for each of N subjects. A set of test data is generated for each phenotype in the database, a distribution of genomic events in windows for each phenotype is computed, and a tensor is extracted for each window that represents a distribution of genomic events for each phenotype. The method includes classifying each phenotype of the test data with a classifier, and assigning a phenotype to a patient.

17 Claims, 9 Drawing Sheets

(51) Int. Cl.
*G06N 7/00* (2006.01)
*G16H 50/20* (2018.01)
*G16B 40/00* (2019.01)

(58) Field of Classification Search
CPC ...... G06N 99/005; G16H 50/20; G16H 50/70; G06F 19/18; G06F 19/24
USPC .......................................................... 706/12
See application file for complete search history.

(56) References Cited

U.S. PATENT DOCUMENTS

| | | | |
|---|---|---|---|
| 2008/0138799 A1* | 6/2008 | Cheng | G16B 40/00 435/6.13 |
| 2008/0187930 A1 | 8/2008 | Shaughnessy et al. | |
| 2009/0165017 A1* | 6/2009 | Syed | G06F 16/10 719/311 |
| 2009/0326832 A1* | 12/2009 | Heckerman | G16B 20/00 702/20 |
| 2011/0055128 A1* | 3/2011 | Heckerman | G16B 40/00 706/13 |
| 2014/0249762 A1 | 9/2014 | Alter | |
| 2014/0297195 A1 | 10/2014 | Keller et al. | |
| 2016/0098519 A1* | 4/2016 | Zwir | G16B 20/00 702/19 |
| 2017/0286594 A1* | 10/2017 | Reid | G16B 20/00 |

OTHER PUBLICATIONS

Park et al., "Deep learning for regulatory genomics"; nature biotechnology vol. 33 No. 8 Aug. 2015; pp. 825-826.

Victoria Hore et al., "Tensor decomposition for multi-tissue gene expression experiments", Europe PMC Funders Group Author Manuscript; Published in final edited form as: Nat Genet. Sep. 2016 ; 48(9): 1094-1100. doi:10.1038/ng.3624.

\* cited by examiner

SINGLE SAMPLE GENETIC CLASSIFICATION VIA TENSOR MOTIFS

BACKGROUND

The present invention generally relates to genomic analysis, and more specifically, to single sample genetic classification via tensor motifs.

In medical contexts, genomic data has the potential to reveal associations between various phenotypes, including associations between observed medical conditions and responsiveness or non-responsiveness to specific medical treatments. Determining the genomic basis of particular traits involves determining correlations between a person's genotype (the particular sequence that makes up the person's genetic code) and the person's phenotype (the expression of the genotype in traits). However, these correlations can be subtle and difficult to discover, with multiple gene sequences playing a role in the expression of certain phenotypes. This complexity is particularly significant when identifying diseases and other disorders, both within a specific person and across entire populations.

SUMMARY

Embodiments of the present invention are directed to a computer-implemented method. A non-limiting example of the computer-implemented method includes generating, by a processor, a set of training data for each phenotype in a database including a set of subjects. The set of training data is generated by dividing genomic information of N subjects selected with or without repetition into windows, computing a distribution of genomic events in the windows for each of N subjects, and extracting, for each window, a tensor that represents the distribution of genomic events for each of N subjects. The method includes generating, by the processor, a set of test data for each phenotype in the database including the set of subjects. The method includes computing, by the processor, a distribution of genomic events in windows for each phenotype of the set of test data. The method includes extracting, by the processor, for each window, a tensor that represents a distribution of genomic events in windows for each phenotype of the set of test data. The method includes classifying, by the processor, each phenotype of the set of test data with a classifier. The method includes assigning, by the processor, a phenotype to a patient using the classifier.

Embodiments of the present invention are directed to a computer program product. The computer program product includes a computer readable storage medium readable by a processing circuit and storing program instructions for execution by the processing circuit for performing a method. A non-limiting example of the method includes generating a set of training data for each phenotype in a database including a set of subjects. The set of training data is generated by dividing genomic information of N subjects selected with or without repetition into windows, computing a distribution of genomic events in the windows for each of N subjects, and extracting, for each window, a tensor that represents the distribution of genomic events in the windows for each of N subjects. The method includes generating a set of test data for each phenotype in the database including the set of subjects. The method includes computing a distribution of genomic events in windows for each phenotype of the set of test data. The method includes extracting, for each window, a tensor that represents a distribution of genomic events for each phenotype of the set of test data. The method includes classifying each phenotype of the set of test data with a classifier. The method includes assigning a phenotype to the patient using the classifier.

Embodiments of the present invention are directed to a processing system for classifying subject genetic data. The processing system includes a processor in communication with one or more types of memory, and the processor is configured to perform a method. A non-limiting example of the method includes generating a set of training data for each phenotype in a database including a set of subjects. The set of training data is generated by dividing genomic information of N subjects selected with or without repetition into windows, computing a distribution of genomic events in the windows for each of N subjects, and extracting, for each window, a tensor that represents the distribution of genomic events in the windows for each of N subjects. The method includes generating a set of test data for each phenotype in the database including the set of subjects. The method includes computing a distribution of genomic events in windows for each phenotype of the set of test data. The method includes extracting, for each window, a tensor that represents a distribution of genomic events in windows for each phenotype of the set of test data. The method includes classifying each phenotype of the set of test data with a classifier. The method includes assigning a phenotype to the patient using the classifier.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

Figure 1:
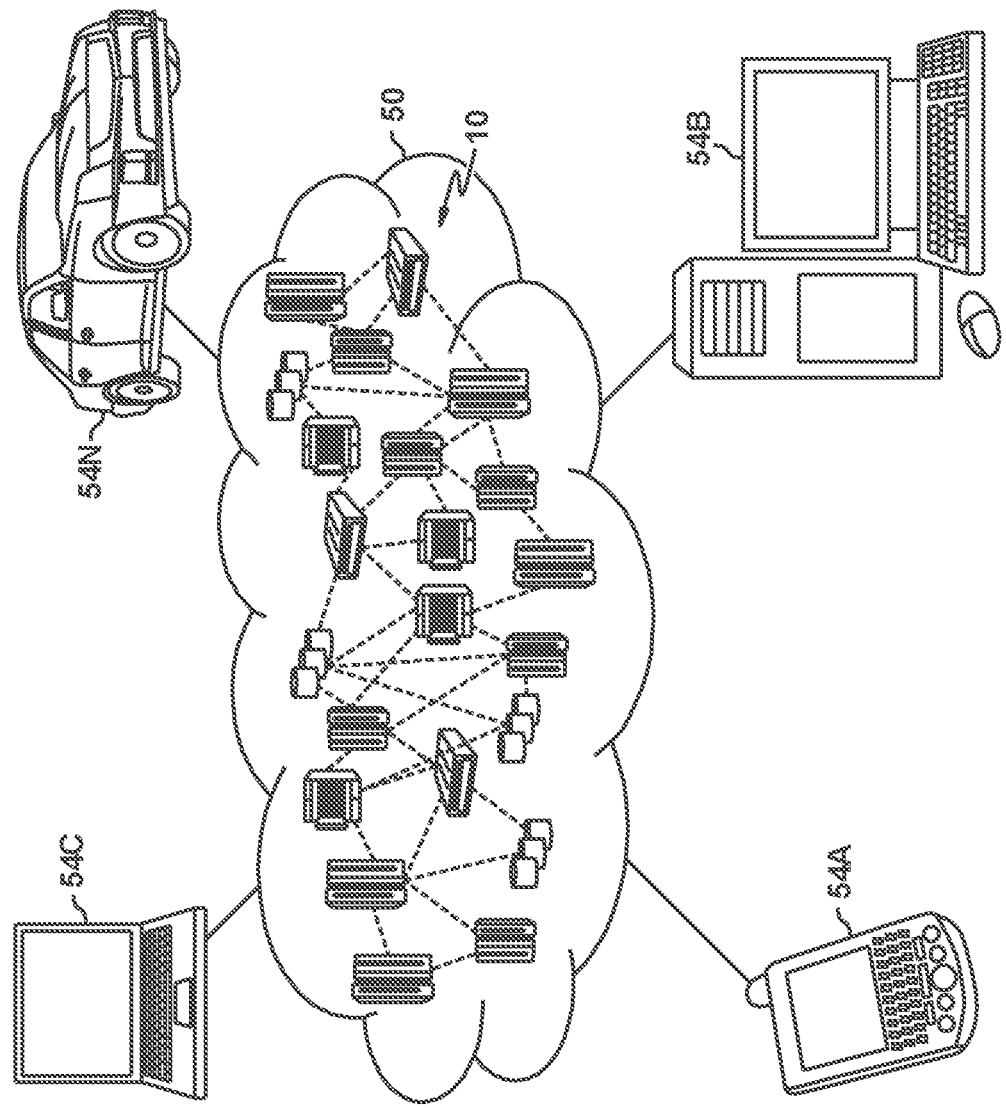
FIG. 1 depicts a cloud computing environment according to an embodiment of the present invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the invention are described herein with reference to the related drawings. Alternative embodiments of the invention can be devised without departing from the scope of this invention. Various connections and positional relationships (e.g., over, below, adjacent, etc.) are set forth between elements in the following description and in the drawings. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. Moreover, the various tasks and process steps described herein can be incorporated into a more comprehensive procedure or process having additional steps or functionality not described in detail herein.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" include any integer number greater than or equal to one, i.e. one, two, three, four, etc. The terms "a plurality" include any integer number greater than or equal to two, i.e. two, three, four, five, etc. The term "connection" includes both an indirect "connection" and a direct "connection."

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

For the sake of brevity, conventional techniques related to making and using aspects of the invention may or may not be described in detail herein. In particular, various aspects of computing systems and specific computer programs to implement the various technical features described herein are well known. Accordingly, in the interest of brevity, many conventional implementation details are only mentioned briefly herein or are omitted entirely without providing the well-known system and/or process details.

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Referring now to FIG. 1, illustrative cloud computing environment 50 according to one or more embodiments of the present invention is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
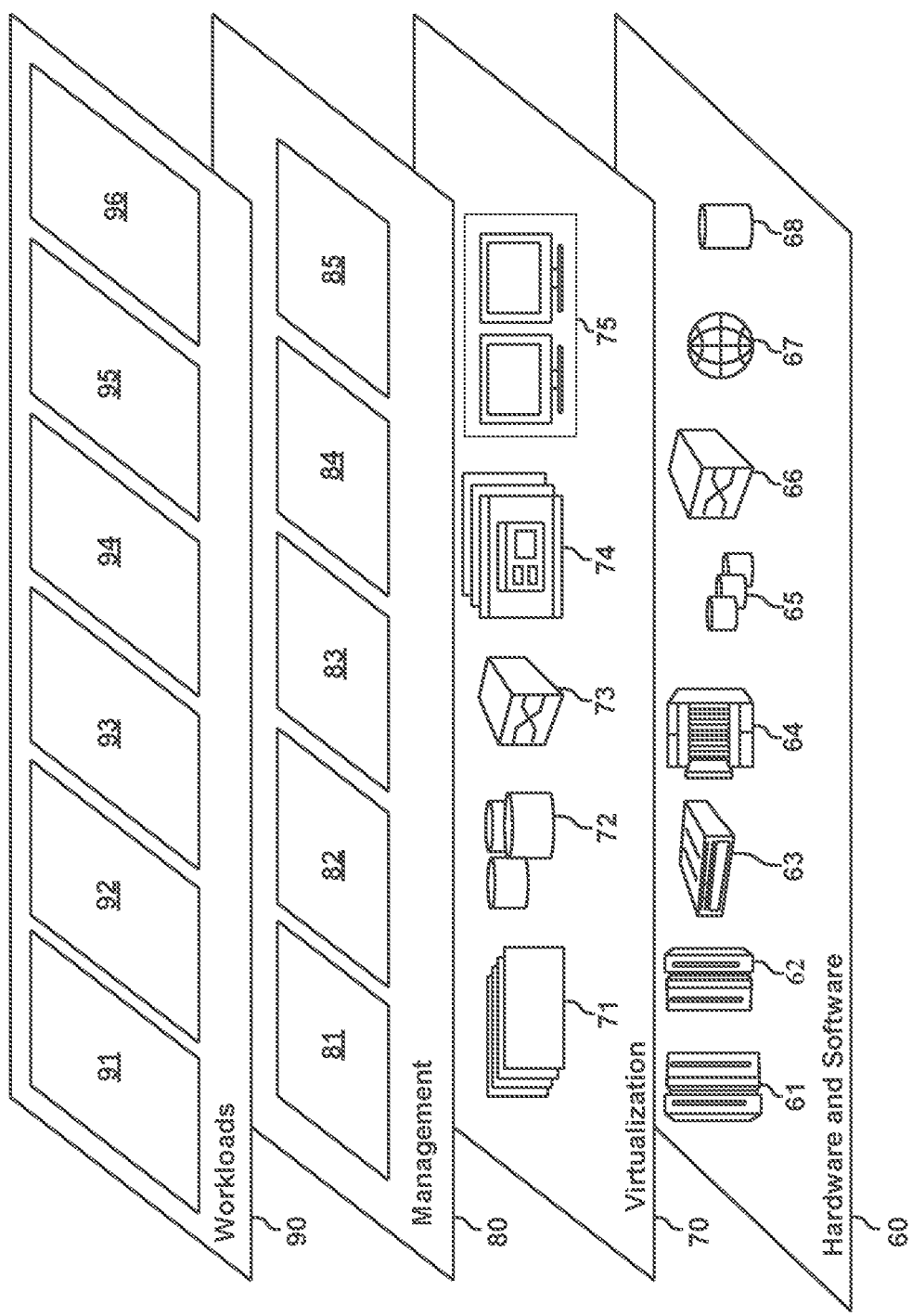
FIG. 2 depicts abstraction model layers according to an embodiment of the present invention.

Referring now to FIG. 2, a set of functional abstraction layers provided by cloud computing environment 50 (FIG. 1) according to one or more embodiments of the present invention is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and genomic analysis 96.

Figure 3:
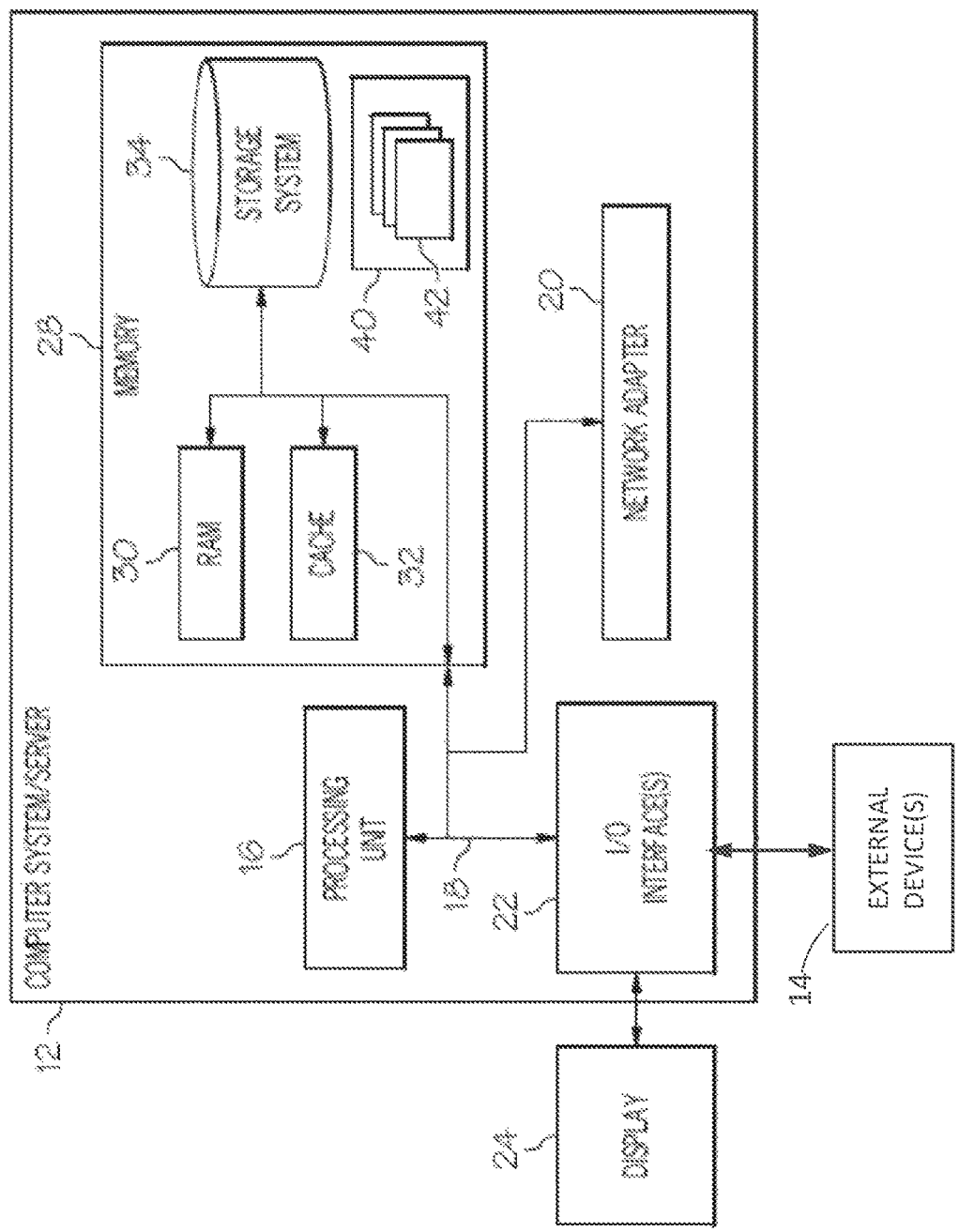
FIG. 3 depicts a block diagram illustrating one example of a processing system for practice of the teachings herein.

Referring now to FIG. 3, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out one or more functions and/or methodologies in accordance with some embodiments of the present invention.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of technologies that are more specifically relevant to aspects of the invention, embodiments of the invention provide non-naïve (or non-trivial) methods of classifying samples of a group for particular phenotypes based at least in part upon genomic data. Genomic and/or chromosomal data is becoming more widely available. Such data has potential to reveal associations between phenotypes, such as diseases or responsiveness to treatment, and genetic data. Thus, analysis of such data could yield data, for example, that can improve the quality of medical care for patients world-wide. However, the size and magnitude of such data and related databases renders the identification of relevant associations computationally difficult.

Turning now to an overview of the aspects of the invention, one or more embodiments of the invention address the above-described shortcomings of the prior art by providing a tensor-based analysis of genetic data to classify samples based upon given phenotypes. Such embodiments can positively impact not only healthcare applications, but also agriculture, biology, food safety and other life-science applications.

The above-described aspects of the invention address the shortcomings of the prior art by providing a flexible approach to determine diagnosis, treatment plans, and prognoses tailored to a patient based on genetic data for a series of patients and personalized data for the patient of interest. A classifier according to embodiments of the invention includes a tensor-based analysis.

Figure 4:
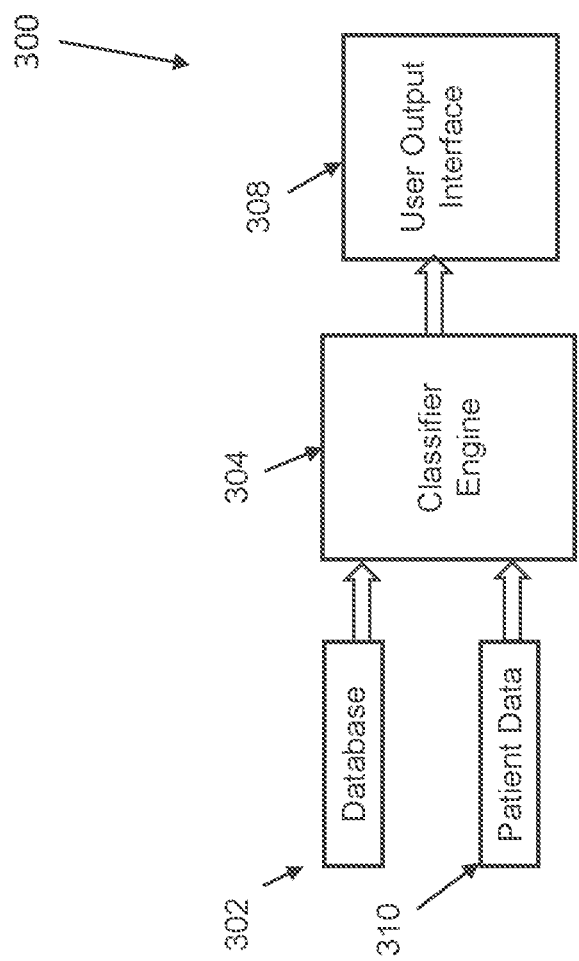
FIG. 4 depicts a block diagram illustrating an exemplary system according to embodiments of the present invention.

Turning now to a more detailed description of aspects of the present invention, FIG. 4 depicts an exemplary system 300 for assigning a phenotype to a patient based on embodiments of the invention. The system 300 includes a database input 302 and a patient data input 310 in communication with a classifier engine 304.

The database includes a set of subjects with a plurality of phenotypes. The set of subjects can have different types of diseases, for example, prostate cancer, breast cancer, colon cancer, etc. The set of subjects also can have subtypes of the same type of disease, for example, subtypes of breast cancer. The information in the database includes, for example, chromosomal sequence data, whole genome data, whole exome data, selected regions of genetic data, such as coding regions of genetic data, non-coding regions of genetic data, and combinations thereof.

Patient (subject) data input 310 includes genetic data for a subject under investigation. The patient data input 310 can include, for example, chromosomal sequence data, whole genome data, whole exome data, selected regions of genetic data, such as coding regions of genetic data, non-coding regions of genetic data, and combinations thereof.

Once the database input 302 and patient data input 310 are received into the system 300, a set of training data and a set of test data are generated for each phenotype in the database. The classifier engine 304 classifies each phenotype of the set of test data using a classifier M. Based on the classification, a phenotype is assigned to the patient. Thus, the classifier M determines whether the genomic information in question indicates the likely manifestation of a particular phenotype.

The system 300 can include a user output interface 308. The user output interface 308 can include a visual output including results of a classification, such as a probability for a phenotype, a confidence interval, and/or an assignment of a subject to a disease.

Optionally, in some embodiments of the invention, the system can add the subject data 310 to the training data 302 to improve future classifications.

Figure 5:
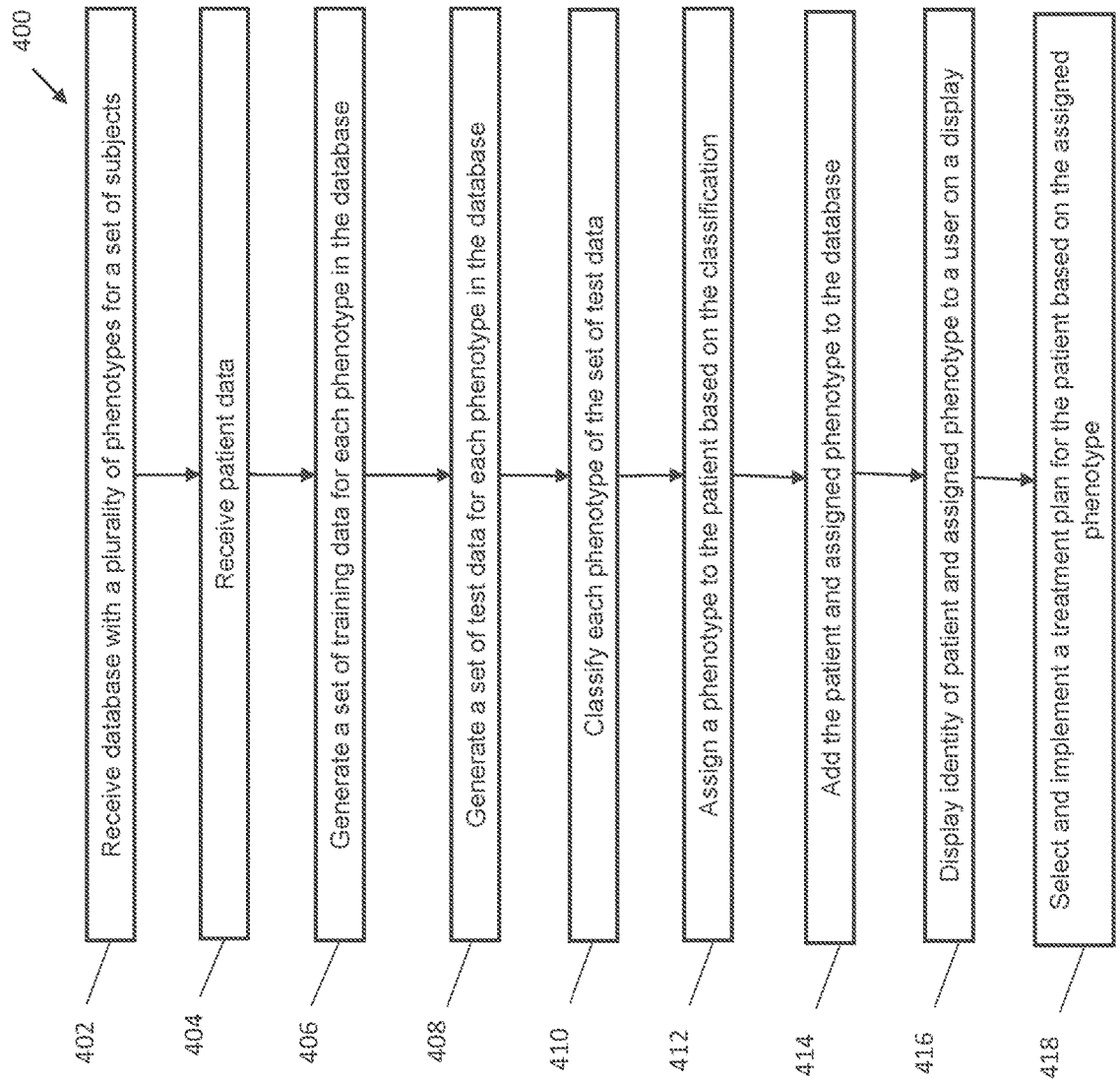
FIG. 5 depicts a flow diagram illustrating an exemplary method according to embodiments of the present invention.

FIG. 5 depicts a flow diagram of an exemplary method 400 for assigning a phenotype to a patient according to embodiments of the invention. The method 400 can be performed by the system 300 shown in FIG. 4.

The method 400 includes, as shown at block 402, receiving a database including a plurality of phenotypes for a set of subjects. The method 400 includes, as shown in block 404, receiving patient data. In addition to genetic data, any available other data on the patient data can be included. For example, the patient's medical history, previous diagnoses by human doctors, list of symptoms and vitals, and other information relevant to the health of the individual can be included. When such additional information is included, subjects can be selected from the database with similar information. For example, when the patient's age is available, subjects with a similar age can be selected from the database to avoid biases.

The method 400 includes, as shown in block 406, generating a set of training data for each phenotype in the database. The set of training data is used to train a machine learning classifier that can, for example, identify the presence of genetic indicators that lead to the expression of a particular phenotype (e.g., disease or genetic condition).

Figure 6:
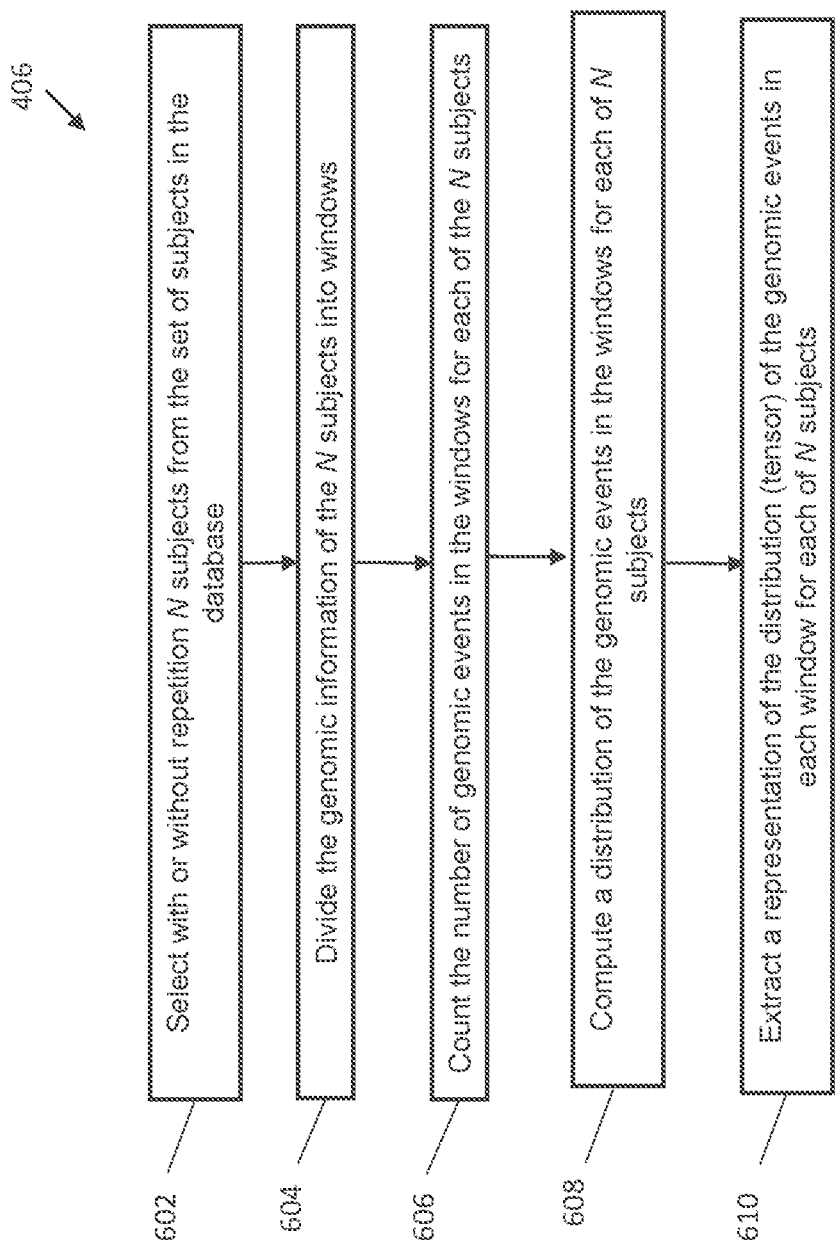
FIG. 6 depicts a flow diagram illustrating an exemplary method according to embodiments of the present invention.

FIG. 6 depicts a flow diagram of an exemplary method 406 for generating a set of training data for each phenotype in the database according to embodiments of the invention. The method 406 includes, as shown in block 602, selecting with repetition or without repetition N subjects from the set of subjects in the database. The selection is optionally performed with repetition such that a given subject genome can be selected more than once for membership in a given set.

The method 406 includes, as shown in block 604, dividing the genomic information of the N subjects into parts, or windows, with or without repetition. For instance, in some embodiments of the invention, genetic data includes cytobands or other windows (selected contiguous sequences of nucleotides) that are split into windows. The size and other characteristics of windows and/or windows can be tailored to the desired application and data types. For instance, in some embodiments of the invention, each window generated is a fixed size. In some embodiments of the invention, windows generated are of variable sizes. In some embodiments of the invention, the windows are overlapping. In other embodiments, the windows are non-overlapping.

The method 406 includes, as shown in block 606, counting the number of genomic events in the windows for each of the N subjects. The method includes, as shown in block 608, computing a distribution of the genomic events in the windows for each of N subjects. An event can be any kind of genetic feature, such as a mutation for example. Other events can include, but are not limited to, copy number variation alteration, gene disruption, and structural variants. For example, in the case of mutations, the distribution can be in the form of a table where each row is a mutation of a subject. The table can also include other information, such as gene identities, deleteriousness of the mutations, possible annotations. In some exemplary embodiments, the distribution is in the form of a graph.

The method includes, as shown in block 610, extracting, for each window, a representation of the distribution (tensor) of the genomic events for each of N subjects. The tensor is a single descriptor of the distribution of the events in each window for each of the N subjects.

The tensor is, for example, an array of length W (i.e., number of windows), where each entry in the array is a representation of the distribution. The tensor can include, for example, a simple n-tuple that encodes a particular statistical feature. For instance, each tensor can include a 4-tuple that includes the mean, variance, skewness, and kurtosis of the distribution relating to a respective window or shingle across the sets. Other methods of constructing tensors are known and can be used in accordance with embodiments of the invention.

Figure 8:
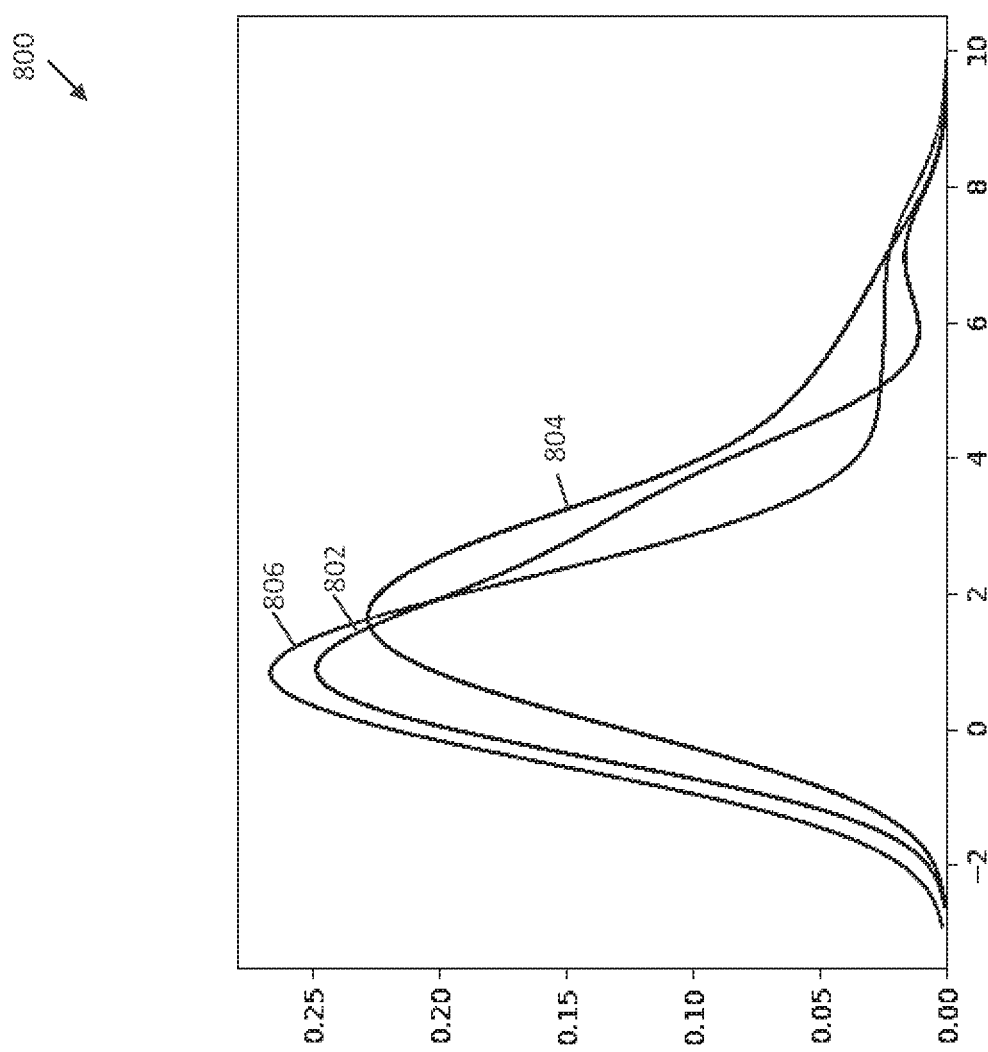
FIG. 8 is a diagram illustrating an exemplary distribution derived from a set of training data.

FIG. 8 is a diagram illustrating an exemplary distribution 800 (tensor) derived from a set of training data. Each curve (curve 802, curve 804, and curve 806) represents a different phenotype. As shown, each phenotype demonstrates a different distribution of genomic events. The shapes and relative features of the curves illustrate the different distributions, which is what is captured by the tensors.

The tensor extracted from the set of training data is used to train a classifier M. The set of training data is used as input in a machine learning process that can be used to determine a model that recognizes correspondences between the input genotypes and known phenotypes. In some embodiments of the invention, the first four moments of each distribution can be constructed into an array, or tensor, as input for a classifier, for instance in a machine learning analysis (e.g., support vector machine processes (SVM), linear discriminant analysis (LDA), random forest methods, and/or Bayesian processes).

Figure 7:
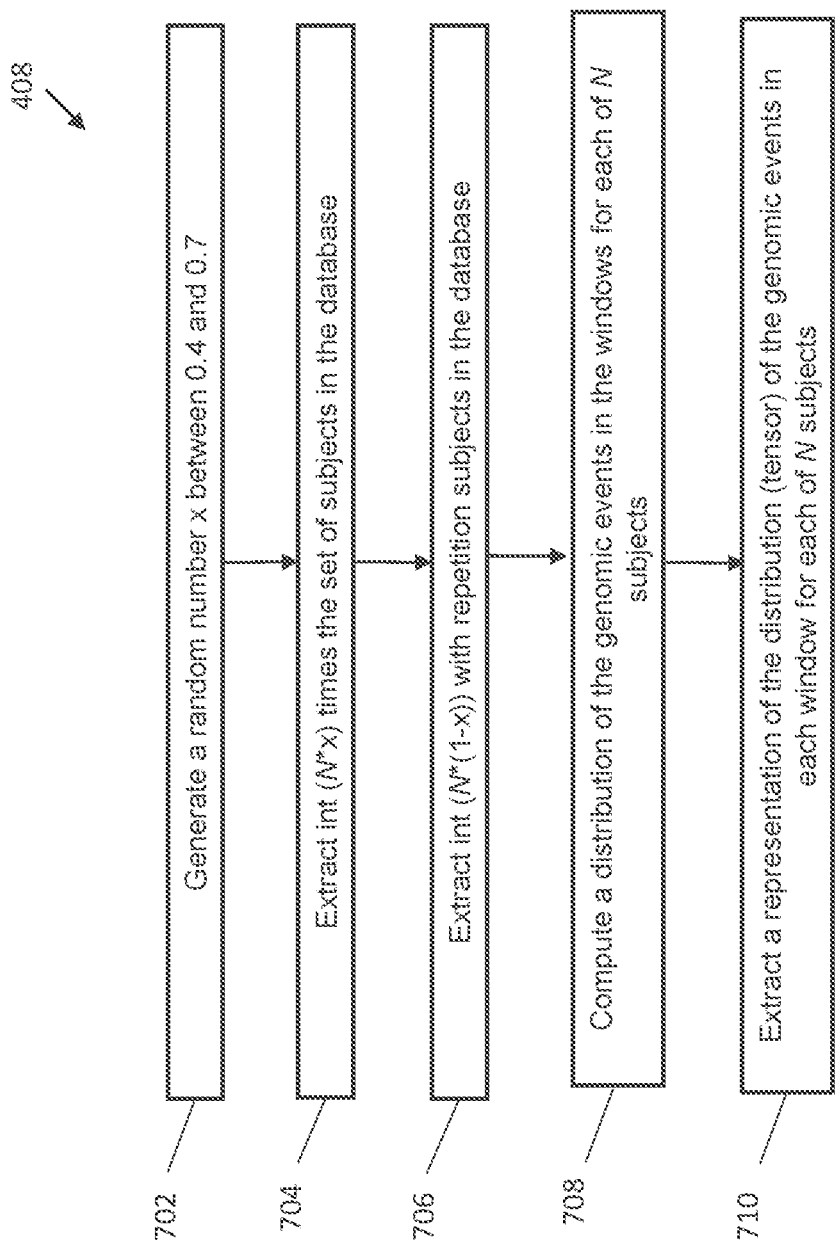
FIG. 7 depicts a flow diagram illustrating an exemplary method according to embodiments of the present invention.

Turning again to FIG. 5, the method 400 includes, as shown in block 408, generating a set of test data for each phenotype in the database. FIG. 7 depicts a flow diagram of an exemplary method 408 for generating a set of test data for each phenotype in the database according to embodiments of the invention. It is to be noted that the exemplary method 408 is but an example, and other methods can be used to generate the set of test data.

The method 408 includes, as shown in box 702 (of FIG. 7), generating a random number x between 0.4 and 0.7. In some embodiments, the number can be fixed, or a different range can be used to generate the random number. The method 408 includes, as shown in box 704, extracting int (N*x) times the set of subjects in the database. The value of N in method 408 can be different than in method 406 used to generate the training data. The method 408 includes, as shown in box 706, extracting int (N*(1−x)) with repetition subjects in the database. The method 408 includes, as shown in box 708, computing a distribution of the genomic events in the windows for each of N subjects. The method 408 includes, as shown in box 710, extracting, for each window, a representation of the distribution (tensor) of the genomic events for each of N subjects.

Turning again to FIG. 5, the method 400 includes, as shown in block 410, classifying each phenotype of the set of test data. Once the classifier M is trained using the set of training data, machine learning then uses the set of test data to test the classifier M. The set of test data generated are provided as input for the trained version of M. The genotypes of the set of test data is analyzed and used to predict the known phenotypes of the set of test data. Disagreements between predictions and the known results are then used as feedback to the model to correct the model and improve its accuracy. In some embodiments of the invention, the classifications can be repeated a number of times sufficient to obtain a confidence interval for the assignment of a subject to one or more diseases.

Figure 9:
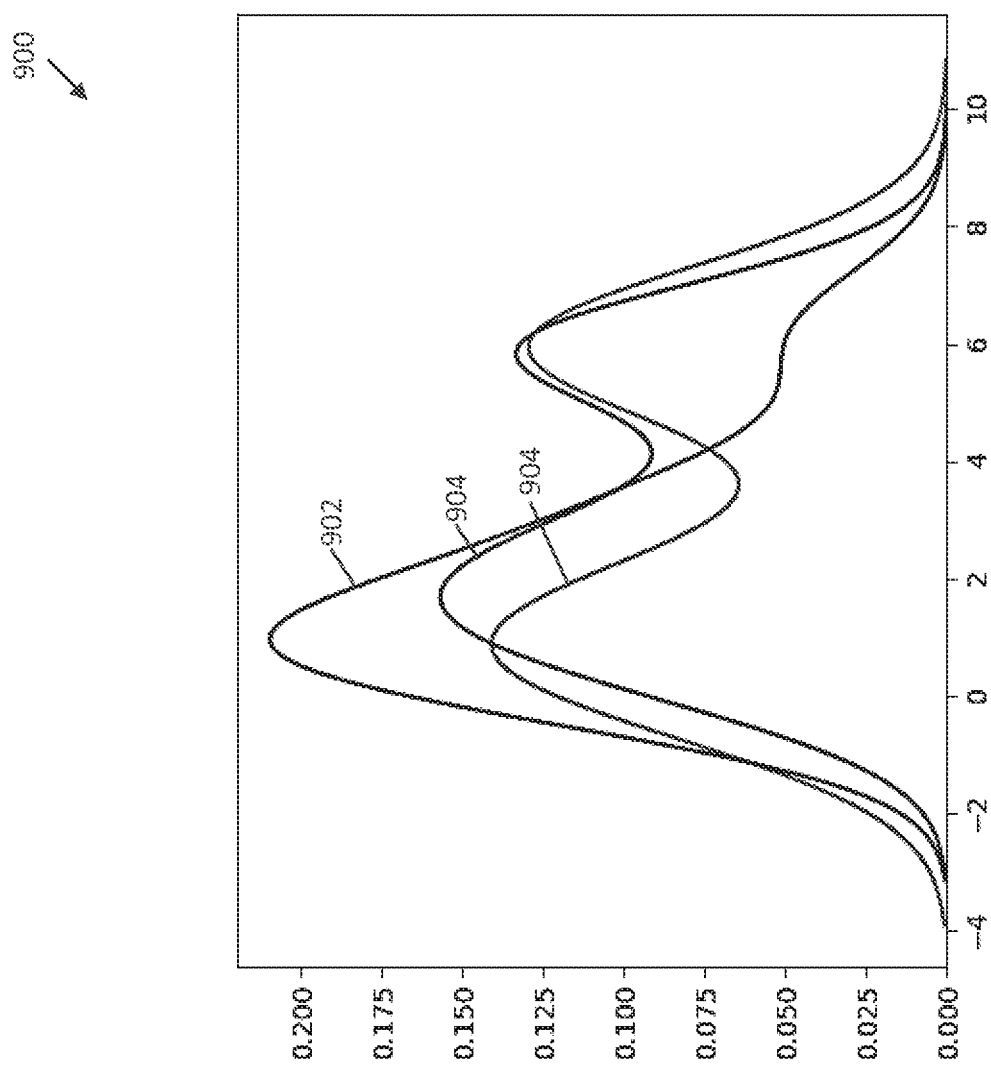
FIG. 9 is a diagram illustrating an exemplary distribution derived from a set of test data.

FIG. 9 is a diagram 900 illustrating an exemplary distribution (tensor) derived from a set of test data. Each curve (curve 902, curve 804, and curve 806) represents a different phenotype. As shown, each phenotype demonstrates a different distribution of genomic events. The shapes and relative features of the curves illustrate the different distributions, which is what is captured by the tensors. When compared to the tensors derived from the training data set (in FIG. 8), the features and relative distributions captured in test curve 902 are most similar to curve 802 (in FIG. 8).

The method includes, as shown in block 412, assigning a phenotype to the patient based on the classification, using the classifier M. The classifier M determines whether the genome in question indicates the likely manifestation of a particular phenotype. Classification can be performed by a variety of methods, including, but not limited to considering the best classification value, a majority vote approach, an expert model, etc.

The method optionally includes, as shown in block 414, adding the patient and assigned phenotype to the database. The method includes, as shown in block 416, displaying the identity of the patient and the assigned phenotype to a user on a display. The method optionally includes, as shown in block 416, selecting and implementing a treatment plan for the patient based on the assigned phenotype. The method can be used for designing treatment plans for the patient based on the assigned phenotype. The treatment plan can be selected and implemented by a physician or other health care personnel. Instructions can be displayed to the physician or health care personnel, with the patient's phenotype and recommended treatment plan. The physician or health care personnel then can diagnose and/or treat the patient as necessary. In some embodiments, once the patient's phenotype is assigned, the patient's prognosis can be accurately determined in addition to, or instead of treatment planning.

Embodiments of the invention can be used to determine, for a patient (subject) having a particular disease, optimal modes of treatment. In some embodiments of the invention, for example, a patient having a known broad category of disease, such as cancer, can be further diagnosed according to embodiments of the invention to improve treatment outcomes. For instance, a genetic analysis can reveal a 99% confidence that the subject has breast cancer.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method, the method comprising:
    generating, by a processor, a set of training data for each phenotype in a database comprising a set of subjects, the set of training data generated by dividing genomic information of N subjects selected with or without repetition into windows, computing a first distribution of genomic events in the windows for each of the N subjects, and extracting, for each window, a first tensor that represents the first distribution of genomic events for each of the N subjects;
    training a classifier on the set of training data;
    generating, by the processor, a set of test data for each phenotype in the database comprising the set of subjects, wherein generating the set of test data comprises generating a random number x between 0 and 1, extracting N*x subjects in the database, and extracting, with repetition, N*(1−x) subjects in the database;
    computing, by the processor, a second distribution of genomic events in the windows for each phenotype of the set of test data;
    extracting, by the processor, for each window, a second tensor that represents the second distribution of genomic events in the windows for each phenotype of the set of test data;
    classifying, by the processor, each phenotype of the set of test data with the classifier;
    updating the classifier based on a comparison of a curve of the first tensor and a curve of the second tensor;
    assigning, by the processor, a phenotype to a patient not found in the database using the classifier;
    adding the patient and assigned phenotype to the database; and
    selecting and implementing a treatment plan to the patient based on the phenotype assigned to the patient.

2. The computer-implemented method of claim 1, wherein the genomic events are mutations.

3. The computer-implemented method of claim 1, wherein the random number x is between 0.4 and 0.7.

4. The computer-implemented method of claim 1, wherein the genomic events are copy number variation alterations, gene disruptions, and structural variants.

5. The computer-implemented method of claim 1, wherein the database includes subjects with different types of diseases or subtypes of a same disease.

6. The computer-implemented method of claim 1, wherein the phenotype is assigned to the patient using a probability and confidence interval.

7. A computer program product for classifying subject genetic data, the computer program product comprising:
    a computer readable storage medium readable by a processing circuit and storing program instructions for execution by the processing circuit for performing a method comprising:
    generating a set of training data for each phenotype in a database comprising a set of subjects, the set of training data generated by dividing genomic information of N subjects selected with or without repetition into windows with or without repetition, computing a first distribution of genomic events in the windows for each of the N subjects, and extracting, for each window, a first tensor that represents the first distribution of genomic events for each of the N subjects;
    training a classifier on the set of training data;
    generating a set of test data for each phenotype in the database comprising the set of subjects, wherein generating the set of test data comprises generating a random number x between 0 and 1, extracting N*x subjects in the database, and extracting, with repetition, N*(1−x) subjects in the database;
    computing a second distribution of genomic events in the windows for each phenotype of the set of test data;
    extracting, for each window, a second tensor that represents the second distribution of genomic events in the windows for each phenotype of the set of test data;

classifying each phenotype of the set of test data with the classifier;

updating the classifier based on a comparison of a curve of the first tensor and a curve of the second tensor;

assigning a phenotype to a patient not found in the database using the classifier;

adding the patient and assigned phenotype to the database; and selecting and implementing a treatment plan to the patient based on the phenotype assigned to the patient.

8. The computer program product of claim 7, wherein the genomic events are mutations.

9. The computer program product of claim 7, wherein the random number x is between 0.4 and 0.7.

10. The computer program product of claim 7, wherein the genomic events are copy number variation alterations, gene disruptions, and structural variants.

11. The computer program product of claim 7, wherein the database includes subjects with different types of diseases or subtypes of a same disease.

12. The computer program product of claim 7, wherein the phenotype is assigned to the patient using a probability and confidence interval.

13. A processing system for classifying subject genetic data, comprising:

a processor in communication with one or more types of memory, the processor configured to perform a method, wherein the method comprises:

generating a set of training data for each phenotype in a database comprising a set of subjects, the set of training data generated by dividing genomic information of N subjects selected with or without repetition into windows with or without repetition, computing a first distribution of genomic events in the windows for each of the N subjects, and extracting, for each window, a first tensor that represents the first distribution of genomic events for each of the N subjects;

training a classifier on the set of training data;

generating a set of test data for each phenotype in the database comprising the set of subjects, wherein generating the set of test data comprises generating a random number x between 0 and 1, extracting N*x subjects in the database, and extracting, with repetition, N*(1−x) subjects in the database;

computing a second distribution of genomic events in the windows for each phenotype of the set of test data;

extracting, for each window, a second tensor that represents the second distribution of genomic events in the windows for each phenotype of the set of test data;

classifying each phenotype of the set of test data with the classifier;

updating the classifier based on a comparison of a curve of the first tensor and a curve of the second tensor;

assigning a phenotype to a patient not found in the database using the classifier;

adding the patient and assigned phenotype to the database; and selecting and implementing a treatment plan to the patient based on the phenotype assigned to the patient.

14. The processing system of claim 13, wherein the genomic events are mutations.

15. The processing system of claim 13, wherein the random number x is between 0.4 and 0.7.

16. The processing system of claim 13, wherein the genomic events are copy number variation alterations, gene disruptions, and structural variants.

17. The processing system of claim 13, wherein the database includes subjects with different types of diseases or subtypes of a same disease.

\* \* \* \* \*